US012609190B2

(12) United States Patent
Freeman et al.

(10) Patent No.: US 12,609,190 B2
(45) Date of Patent: Apr. 21, 2026

(54) METHOD AND EQUIPMENT FOR IMPROVING CARDIAC ARREST RESUSCITATION (POCKET CRASH CART)

(71) Applicants: Tamara Aliza Freeman, Litchfield, NH (US); Michelle Alyssa Freeman, Litchfield, NH (US)

(72) Inventors: Tamara Aliza Freeman, Litchfield, NH (US); Michelle Alyssa Freeman, Litchfield, NH (US)

(*) Notice: Subject to any disclaimer, the term of this patent is extended or adjusted under 35 U.S.C. 154(b) by 314 days.

(21) Appl. No.: 18/377,005

(22) Filed: Oct. 5, 2023

(65) Prior Publication Data

US 2025/0118408 A1 Apr. 10, 2025

(51) Int. Cl.
*A61B 5/363* (2021.01)
*G16H 20/17* (2018.01)

(52) U.S. Cl.
CPC ............. *G16H 20/17* (2018.01); *A61B 5/363* (2021.01)

(58) Field of Classification Search
CPC ......... G16H 20/17; G16H 20/10; A61B 5/363
See application file for complete search history.

(56) References Cited

U.S. PATENT DOCUMENTS

| | | | | |
|---|---|---|---|---|
| 5,674,190 | A * | 10/1997 | Kelly | A61M 1/369 607/106 |
| 10,220,161 | B2 * | 3/2019 | Green | A61M 5/142 |
| 12,437,592 | B2 * | 10/2025 | Poddar | A61J 7/0084 |
| 2007/0035403 | A1 * | 2/2007 | Krishna | G08B 25/016 340/573.1 |
| 2011/0099031 | A1 * | 4/2011 | Nair | G16H 40/67 704/235 |
| 2015/0005703 | A1 * | 1/2015 | Hutchinson | A61M 5/14 604/95.01 |
| 2018/0264195 | A1 * | 9/2018 | Hopkins | A61M 5/31513 |
| 2020/0305805 | A1 * | 10/2020 | Freeman | A61B 5/02055 |
| 2022/0061648 | A1 * | 3/2022 | Vasan | A61B 1/042 |
| 2022/0395457 | A1 * | 12/2022 | Lyman | A61K 31/137 |
| 2023/0410968 | A1 * | 12/2023 | D'Albini | G16H 50/20 |

* cited by examiner

*Primary Examiner* — Catherine M Voorhees

(57) ABSTRACT

Method and equipment for improving cardiac arrest resuscitation (Pocket Crash Cart) includes:

1. Manual or Automatic Pocket Crash Cart which attaches to the patient via IV/OS to allows quick and accurate administration of emergency medication manually or remotely.
2. The software for mirroring display screen of manual defibrillator or AED/computer/laptop/phone and video cameras allowing to transfer patient information from the Cardiac Arrest scene especially in hard-to-reach locations (cruise ship, expeditions) to CMF via internet for expert advice and/or administration of emergency medication in the absence of ASLC provider.

15 Claims, 5 Drawing Sheets

Manual PCC dose window (mg)

injection button medicine reservoir

201

201A

203A epinephrine    1.0 amiodarone    300 atropine    1.0

202

201B

201C

203B

203C dose knob multiport IV tubing

METHOD AND EQUIPMENT FOR IMPROVING CARDIAC ARREST RESUSCITATION (POCKET CRASH CART)

BACKGROUND OF THE INVENTION

Field of Invention

This invention relates generally to the resuscitation process during sudden Cardiac Arrest (CA), more specifically to CA in rural or hard to reach locations. This method would aid emergency responders in administering emergency medication.

Cardiac arrest occurs when the heart's electrical transmission system malfunctions due to underlying diseases such as heart attack, heart failure, arrhythmias, cardiomyopathy, ventricular fibrillation, and prolong Q-T syndrome. As a result, the heart stops beating suddenly, which stops blood flow to a person's organs. This can cause a person to stop breathing and lose consciousness, leading to disability or death if not treated immediately.

Sudden Cardiac Arrest can happen to any person in any place. Hence, there is a need for a tool that can allow Emergency Medical Services (EMS) personnel to quickly administer appropriate medication to avoid delays in treatment.

Description of the Prior Art

The current practice for treating CA outside of a hospital setting is for responders to first assess the collapsed individual for absence of consciousness, heartbeat, and/or breathing. Then, responders can call 911 to call EMS to the scene. Then, initial responders can start cardiopulmonary resuscitation (CPR), which can include chest compression, rescue breathing, and using a defibrillator. Defibrillators can be automated (AED) or manual (md), and these devices analyze/display heart rhythms and identify if electric shock is suggested. Once EMS providers arrive, they are equipped and trained to provide CPR. Some are Advance Cardiac Life Support (ACLS) certified, which allows them to administer emergency cardiac medications.

The primary problem with conventional CA diagnostic tools and medication administration is the time it takes for appropriately trained EMS personnel to arrive at the scene of the CA and go through the appropriate life-support steps.

After arriving at the scene and confirming that the person has no pulse and/or isn't breathing, EMS personnel will continue CPR. EMS personnel will also establish intravenous (IV) or intraosseous (IO) access on the patient and connect them to oxygen. Then, if an ACLS certified provider is present, they will retrieve a crash cart (a portable cart that contains all necessary equipment and medications to help with the resuscitation process) from the ambulance to administer emergency medication.

EMS teams may be equipped with a manual defibrillator (md), which gives more options to properly treat CA by displaying the patient's cardiac rhythm on the screen and allowing manual adjustments of how many Joules are delivered during the electrical shock that restarts the heart's electrical system.

An important stipulation to this response plan is that ONLY medical doctors (MD) or ACLS personnel can identify cardiac rhythms on the manual defibrillator and administer appropriate medication. This responder's tasks include:

Opening the appropriate drawer in the crash cart

Locating and opening the vial with the appropriate medication

Withdrawing the appropriate amount of medicine into a syringe

Attaching the syringe to the patient's IV/IO access

Administering the medication and flushing with Normal Saline

This process is repeated for every medication that needs to be administered. For this process to take place, it requires an ACLS provider or the MD to be present and concentrated ONLY on this role.

Through this conventional treatment method, in-hospital CA has a survival rate of around 24%, while out-of-hospital CA survival rate is around only 6%.

In this respect, the proposed method and equipment for improving cardiac arrest resuscitation departs substantially from conventional methods of CA resuscitation process and compositions of the prior art. In doing so, the proposed method provides a quick and accurate assessment of various CA scenarios and provides treatment to increase survival rate and decrease complications to patients with CA.

SUMMARY OF THE INVENTION

In contrast to the known methods of CA resuscitation described in the prior art, the present invention improves medical intervention during medical emergencies/events by ensuring prompt medicine delivery and improving the speed at which care may be given.

The general purpose of the present invention is to provide an improved emergency treatment for cardiac arrests that has many novel features and functions, which is not anticipated, rendered obvious by any of the prior art methods either alone or in any combination thereof.

As described in the Prior Art section, it is an extremely time-consuming process to administer medication using a crash cart. This invention addresses this by containing the medication in a compact device that is convenient to attach to the patient and allows for quick and accurate adjustments in administration.

The secondary aim of this invention is to provide a communication tool and allow EMS responders without ACLS training to better help patients. To attain this, the present invention generally comprises the process of EMS collecting data at the accident site and transferring these findings to a central medical facility through a communication system. Then, an MD or ACLS provider will analyze the data, determine the necessary actions, and communicate the results to the EMS on site. Based upon the displayed results, first responders or EMS team can then make an informed decision regarding the proper treatment of the patient.

The present invention allows for health care providers around the world to have instant access to highly qualified cardiologists, MD or ACLS personnel and start treating CA with medical advice as quickly as possible.

Each computer used by EMS personnel or in the hospital would be able to communicate with the central medical facility using this invention, thereby allowing health care providers at all levels to provide accurate patient assessment and care.

There are additional features of the invention that will be described hereinafter and that will form the subject matter of the claims appended hereto.

In this respect, before explaining the invention in detail, it is to be understood that the invention is not limited in its application to the details of construction and to the arrangements of the components set forth in the following description or illustrated in drawings. The invention is capable of other embodiments and of being practiced and carried out in various ways. Also, it is to be understood that the phraseology and terminology employed herein are for the purpose of the description and should not be regarded as limited.

The primary object of the present invention is to provide quick and accurate administration of medication that may provide life-saving treatment to patients.

The secondary object of the present invention is to provide a CA resuscitation system that will overcome the shortcomings of the prior art.

Another object is to provide a system that provides a quick and accurate assessment of the various CA scenarios and accurate heart rhythm identification.

An additional object is to provide a resuscitation system that may be utilized by health care providers in various locations throughout the world.

The further object is to provide a resuscitation system that utilizes central, secondary, or tertiary health care facility providers to participate in CA.

Another object is to provide a CA diagnostic system that increases the accuracy of the medical diagnosis of the patients.

An additional object is to provide a CA resuscitation system that provides a diagnosis based upon data collected immediately at the emergency site.

A further object is to provide a CA resuscitation system that instantly displays the diagnostic results and clearly communicates between the EMS team and MD/ACLS provider at the central facility.

Another object is to provide a remotely CA resuscitation medical treatment at the site by MD/ACLS provider from the central facility utilizing a communication system.

Other objects and advantages of the present invention will become obvious to the reader, and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific use illustrated and described within the scope of the appended claims.

DETAILED DESCRIPTION OF INVENTION

Figure 1:
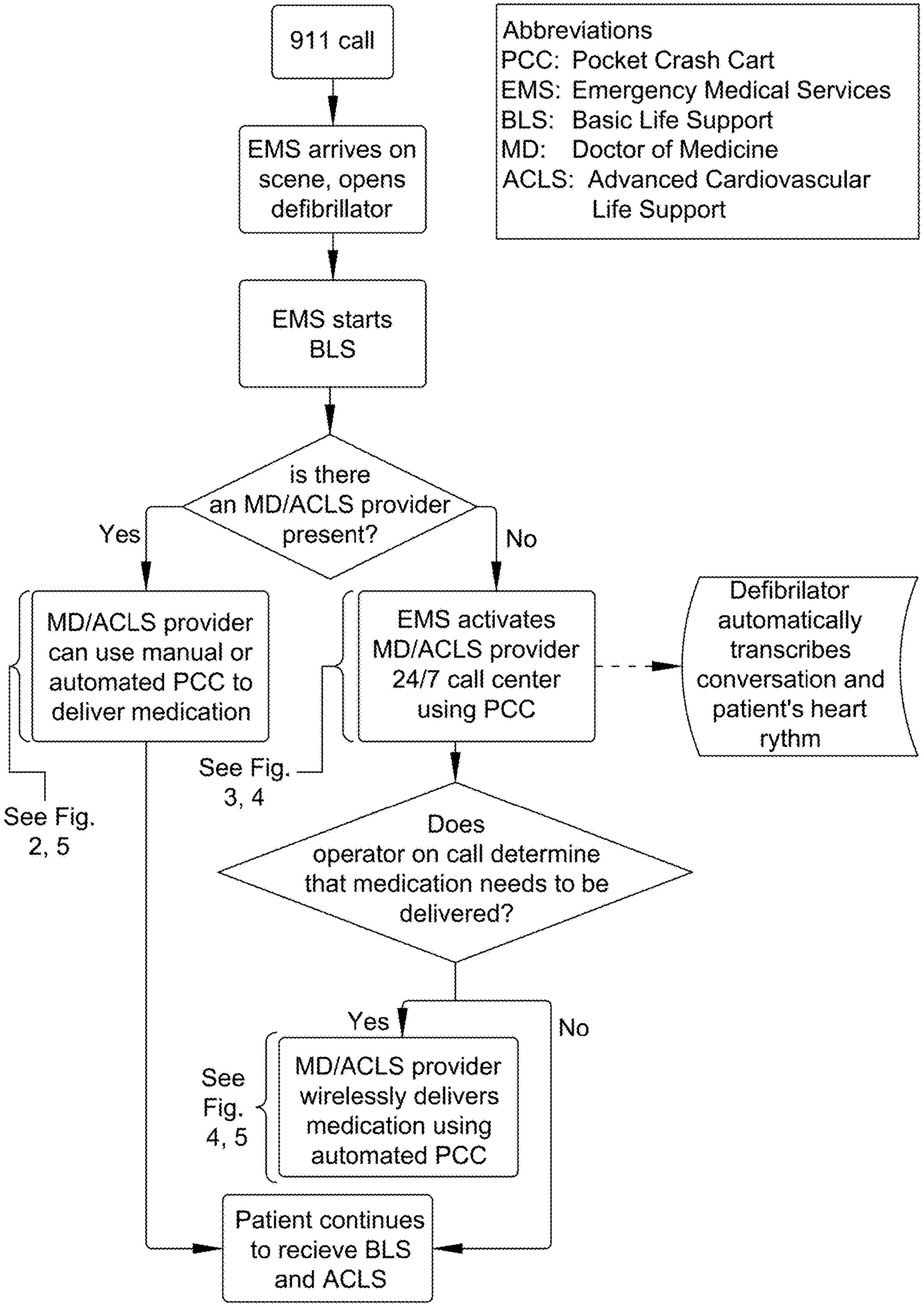
FIG. 1 is a diagram describing an improved method of cardiac resuscitation using the Pocket Crash Cart (PCC) outside of hospital settings (in hospital: Code Blue team instead of EMS arrive).

FIG. 1 explains in detail the improved method of treating CA outside of a hospital setting. When an individual collapses, the first responder starts CPR and calls a 911 center, which dispatches an EMS team.

Figure 3:
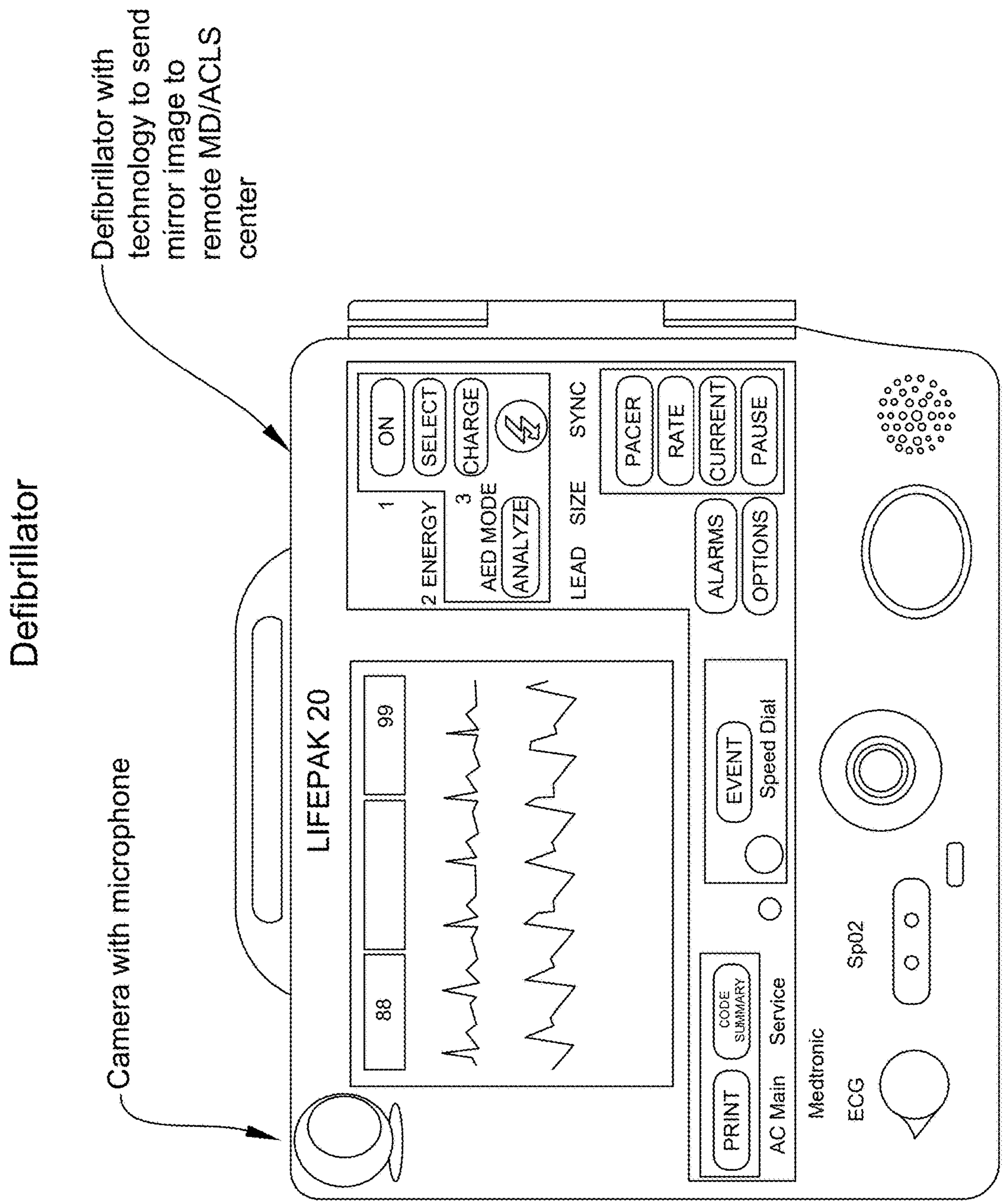
FIG. 3 is a manual defibrillator (md) with a video camera, microphone, speech recognition software, software to mirror the monitor screen, and display for notes.

EMS team follows Basic Life Support (BLS) protocol, assessing the patient for breathing and heartbeat, providing CPR, inserting intravenous catheter (IV) or OS, and applying the oxygen and AED/md pads (FIG. 3). Turning on the defibrillator will immediately connect the EMS team via Internet to a Central Medical Facility (CMF), alerting a MD/ACLS provider that a CA is suspected.

Manual defibrillators (md) can be equipped with video cameras that have speech recognition microphones, mirroring software to record the cardiac arrest event (FIG. 3) and communicate with CMF.

Figure 4:
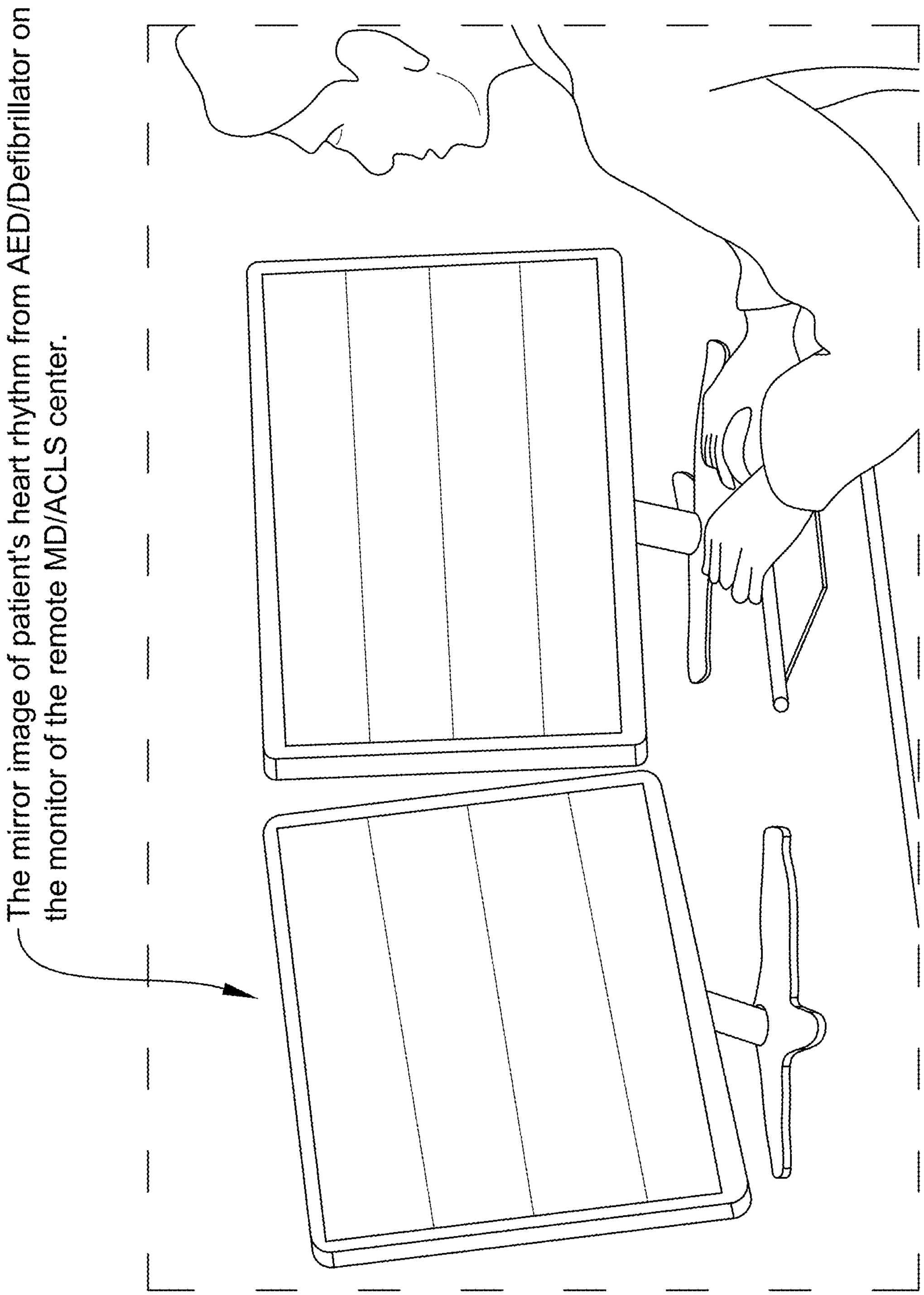
FIG. 4 is a medical/911 center with MD/ACLS personnel trained in cardiac resuscitation, monitoring cardiac arrest events via camera and or mirroring AED/md screen.
Figure 5:
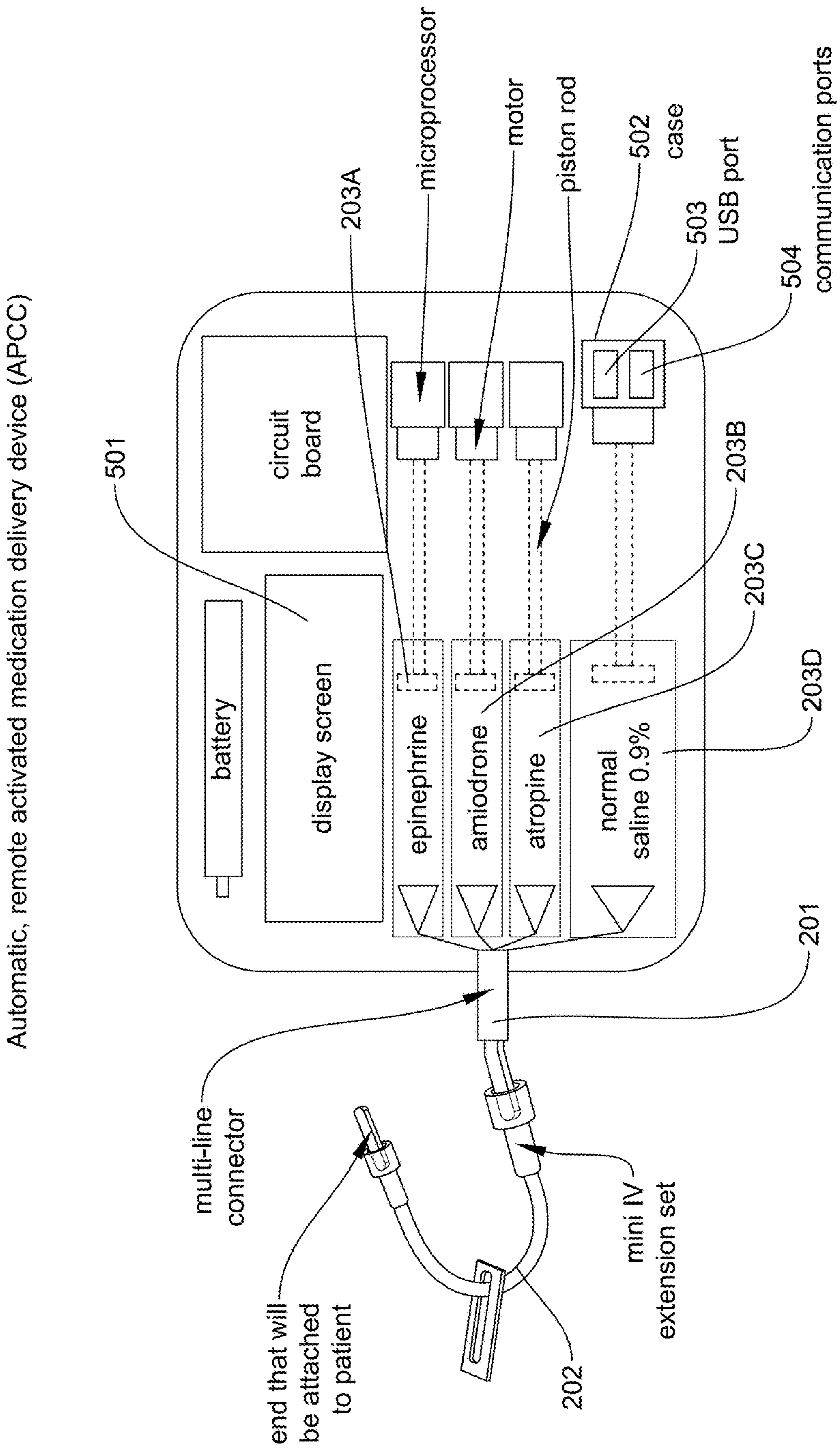
FIG. 5 is automatic, remote activated medication delivery device (PCC) diagram consisting of delivery mechanism, battery, software chips, and vials with cardiac medications.

The camera with microphone can be attached to the EMS personnel or be placed on the scene, but its position must provide a very good angle of the defibrillator so that the cardiac rhythm can be identified by the MD/ACLS provider remotely. This is why the camera (or software for mirroring defibrillator display to the computer screen on the EMS device and on the medical center device (laptop, tablet, computer, etc.)) on the defibrillator is preferred, so it will send the image directly from their screen and the two-way messages can be displayed in one place (FIG. 4).

The AED can be equipped with a video camera to record the event and communicate with CMF, which would allow quick assessment by MD/ASLC provider. The video camera would not only record the events of the cardiac arrest, but also transcribe spoken words to the typed log (which now means you don't need the "recorder" on your ACLS team). These notes can be reviewed on the defibrillator monitor or on the computer screen in a CMF by the Team Leader (MD or ACLS provider) in FIG. 4.

As soon as the video camera on the defibrillator or AED turns on, the microphone will also turn on and sync to the computer (or another device such as a laptop, tablet, phone, etc.).

At the site of the accident, examples of data that can be collected are cardiac rhythm, oxygen saturation, communication, and brief history from witnesses or description of the scene. This data will immediately be transferred to the CMF through a communication system, and then the MD/ACLS provider can conduct analysis, determine the best treatment, and communicate back to the EMS team on the scene using the monitor/laptop/phone/etc.

This invention also involves a system to administer medication on site, using the Pocket Crash Cart (PCC). During cardiac arrest, the most often used medications are:

- Epinephrine IV/IO: 1 mg is given every 3-5 minutes to treat tachycardia, ventricular fibrillation (VF), and ventricular tachycardia (VT).
  - Epinephrine (adrenaline) is a hormone produced by the human body and is responsible for peripheral vasoconstriction to concentrate the blood around the brain and the heart. Epinephrine also strengthens cardiac contractions and increases the chance of the heart returning to a normal rhythm.
- Amiodarone IV/IO: the first dose is 300 mg, and after 15 minutes, the second dose is 150 mg.
  - Amiodarone is another important medication usually given to slow the heart for ventricular fibrillation and ventricular tachycardia (the most common cause of cardiac arrest) if electrical defibrillation is unsuccessful.
- Atropine IV/IO: 1.0 mg every 3-5 minutes is given to treat bradycardia
  - Atropine blocks the effect of the Vagus nerve which slows the heartbeat and acts on the conduction system of the heart and accelerates the transmission of electrical impulses through cardiac tissue.

Other medications can be added to the Pocket Crash Cart if needed.

The manual version of the PCC is good for advanced medical settings with limited ACLS responders. The manual PCC is comprised of multi-port IV tubing with attached prefilled color-coded syringes with epinephrine, amiodarone, and atropine. An example of the amounts of each medication is explained below. These medications can be stored at room temperature.

1. epinephrine: 10 mg, which will allow for 10 bolus administrations
2. amiodarone: 450 mg, which is enough for 2 bolus administrations (first: 300 mg, second: 150 mg)
3. atropine: 3 mg, which will allow for 3 bolus administrations The amount and concentration of each medication can vary. The syringes are attached to the IV line with one port connected to Normal Saline 0.9% IV bag for flush (FIG. 2).

Figure 2:
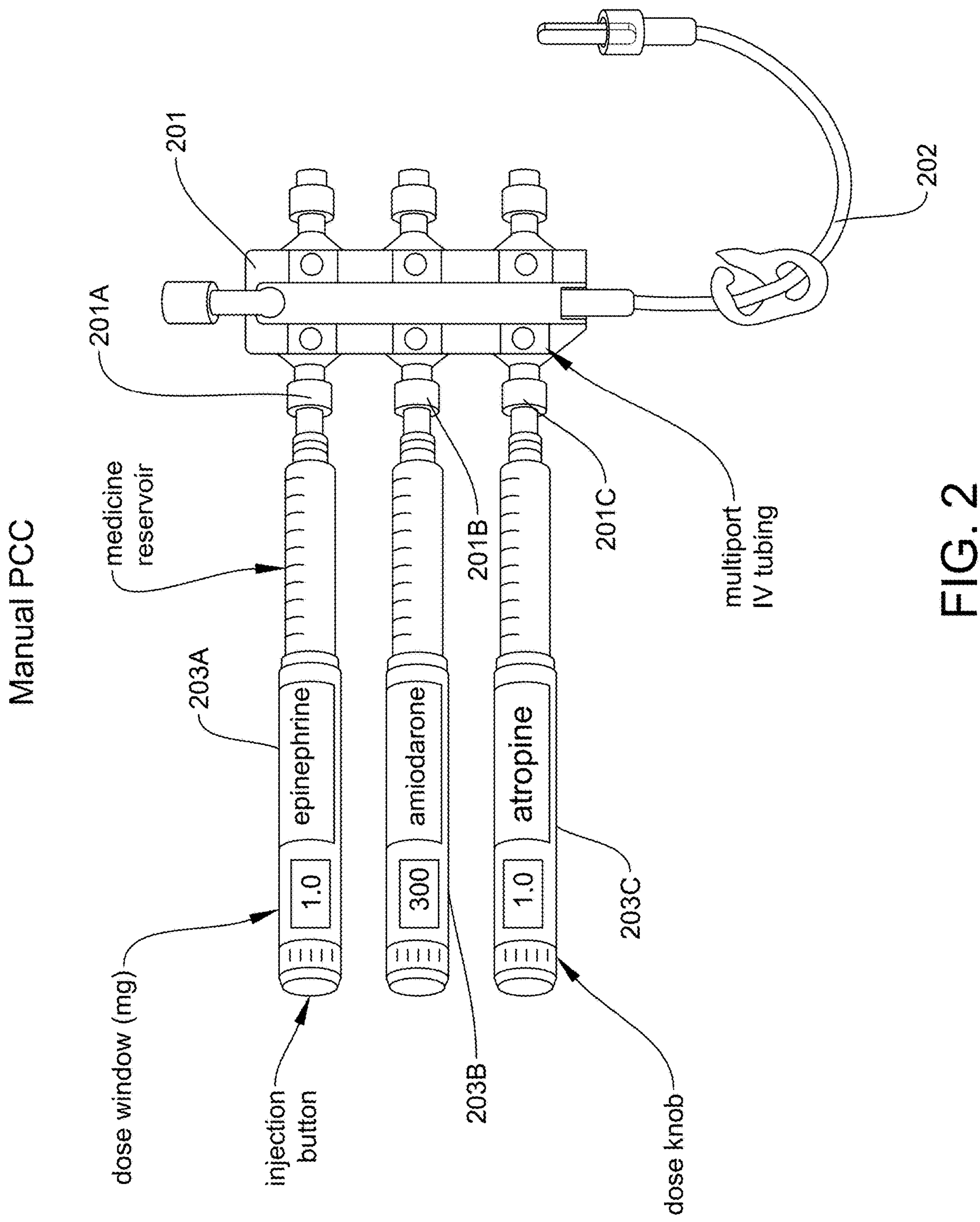
FIG. 2 is a manual Pocket Crash Cart containing multiport IV cannulas with attached color-coded prefilled syringes with medication.

Each syringe (pen body) shown in FIG. 2 consists of a cartridge holder with the medicine, plunger, dose knob, dose window with the dose indicator, and IV connection port with seal.

This device can be suitable for pediatric use as well if the dose indicator is calibrated in 0.01 mg.

After establishing IV/OS on the patient, the PCC is attached to the IV/OC port. Depending on the cardiac heart rhythm and patient condition, the MD/ASLC provider can decide which medication(s) to administer. Then, they can administer the medication(s) directly at the scene by turning the dose indicator to reach appropriate medication dose and then pushing the knob to administer. They can announce the dose and time of administration, allowing the voice recognition software mentioned above to transcribe their speech on the computer screen. This information can be sent to the CMF for record-keeping and to continue to monitor the patient's response to the interventions.

During CA, the medication can be administrated without leaving the patient to open the currently used crash cart and manually attaching the appropriate syringe to the line. So, the current invention saves time and resources to allow first responders to resume CPR more rapidly after medication administration.

An Automatic version of this invention would allow remote administration of the aforementioned medications, such as by using a phone or phone-like device at the scene. These medications may also be remotely administered by ACLS providers at the CMF once they assess the cardiac rhythm of the patient and determine the dose necessary. They may press a button on their laptops/computers/phones, and the Automatic Pocket Crash Cart will administer the proper amount of medication.

An improved Cardiac Arrest Resuscitation process provides accurate information about the patient before admitting to the Emergency Room (ER) at the hospital based upon data accumulated from the accident site, comprising the steps of acquiring accident data performed by an EMS team or first responder at the accident site such as patient information, a brief description of the accident site, and any witnesses or family information. Said accident data is entered into an on-site computer via a video camera and speech recognition software. Said accident data is transferred from the on-site computer to a Central Medical Facility (CMF) computer. Said accident data is analyzed by an MD or ACLS provider. A diagnosis is developed based upon said accident data. Said cardiac arrest diagnosis is transferred to a second computer located at the ER. The MD or ACLS provider sends orders to administer medication via a manual Pocket Crash Card (PCC) to the EMS team at said accident site or administers medications using an Automatic Pocket Crash Card (APCC) themselves at the appropriate time. Results are displayed on the on-site computer monitor at the accident site for the EMS team to review and continue the resuscitation process.

In certain implementations, heart rhythm is utilized to analyze the extent of heart damage as part of the diagnosis.

In certain implementations, the heart rhythm diagnosis includes a visual display of EMS team to MD or ACLS provider communications.

In certain implementations, the heart rhythm diagnosis includes real-time monitoring of the accident scene.

In certain implementations, heart rhythm diagnosis is performed prior to admission of a patient to an ER based upon data accumulated from the accident site, comprising acquiring accident data performed at least at the accident site and within an EMS vehicle, wherein said accident data includes accident site information, patient information, physical environment information, interventions, and medication administration. Said accident data is entered into a first computer associated with the EMS team. Said accident data is transferred from said first computer to a central medical facility with 24/7 coverage. Said accident data is analyzed. A heart injury diagnosis is developed based upon said accident data. The MD or ACLS provider sends orders to administer medication via a manual PCC to the EMS team at said accident site or administers said medication themselves at the appropriate time. Said results are displayed on the first computer monitor at the accident site for the EMS team to review and continue the resuscitation process. Said cardiac arrest diagnosis is transferred to a second computer located at the ER, wherein said step of analyzing said accident data is based on collected information and video monitoring.

In certain implementations, the process includes a defibrillator equipped with a video camera, voice recognition software, mirroring display software, internet access, and a display for notes.

The defibrillator is configured to display and analyze heart rhythm data to advise for an electric shock, wherein the number of joules can be adjusted. The defibrillator displays EMS team communication and transfers heart rhythm data and acquired accident data from the accident site to an EMS team computer. The EMS team computer transfers acquired data to the central medical facility for MD or ACLS provider review. The defibrillator displays and analyzes heart rhythm data synchronized for transcutaneous pacing. The defibrillator displays communication notes.

In certain implementations, the process includes an EMS team computer, including a laptop, phone, tablet, or pad, which can be equipped, instead of or in addition to the defibrillator, with a video camera, voice recognition software, mirroring display software, and internet access. The EMS team computer acquires data from the accident site, including accident site information, patient information, physical environment information, interventions, and medication administration. The EMS team computer transfers said data to a secondary computer at a central medical facility with 24/7 coverage and receives feedback from an MD or ACLS provider.

In certain implementations, the process includes a manual Pocket Crash Card.

The manual Pocket Crash Card includes a multi-port needleless intravenous connector with integrated check valves and slide-clamp tubing configured to be attached to a patient's intravenous line. The manual Pocket Crash Card further includes at least three color-coded syringes containing emergency medications. A red-colored syringe is filled with epinephrine, wherein red indicates stop tachycardia, for example 10 mg, allowing for multiple bolus administrations. A yellow-colored syringe is filled with amiodarone, wherein yellow indicates stop tachycardia, for example 450 mg, sufficient for two bolus administrations including a first bolus of 300 mg and a second bolus of 150 mg. A green-colored syringe is filled with atropine, wherein green indicates increase heart rate with bradycardia, for example 3 mg, allowing for multiple bolus administrations. One port of the connector is attached to a 0.9% normal saline intravenous bag or syringe for flushing.

Each syringe includes a syringe body with a dose window, a dose indicator, a dose knob, a rubber seal, and a label. Inside the syringe body is a cartridge holder and a plunger. To administer medication, a user chooses an appropriate syringe, turns the dose knob to select an appropriate dose depending on the heart rhythm displayed on the defibrillator, and pushes the dose knob until it stops and a zero value is displayed in the dose window. The line is flushed with 0.9% normal saline by opening the slide clamp. The syringe body with the dose window and dose indicator may be calibrated to pediatric doses to expand the use of the Pocket Crash Card.

In certain implementations, the process includes an Automatic Pocket Crash Card.

The Automatic Pocket Crash Card includes a pump configured to deliver appropriate medication to a patient and a user interface including a processor and a display. The Automatic Pocket Crash Card includes a water-resistant enclosed apparatus containing a cassette comprising medication vials attached to the pump and a delivery mechanism, a battery, a processor, Bluetooth capability, communication interfaces, and USB ports. The Automatic Pocket Crash Card allows manual entry of patient clinical status information via the user interface to choose appropriate medication and dosage, wherein the date and time are recorded and displayed on the screen for monitoring. The patient's clinical status information is downloaded into the central medical facility system via a communication port. The communication port may be a wireless communication port configured to communicate with a central medical facility computer, screen, laptop, or phone. The user interface may be part of the medical infusion pump or may be part of a device remote from the medical infusion pump. Based on received patient clinical information, including heart rhythm data indicating medical intervention, medication may be administered manually or remotely.

We claim:

1. An improved Cardiac Arrest Resuscitation (CAR) process that provides accurate information about the patient before admitting to the Emergency Room (ER) at the hospital based upon data accumulated from the accident site, comprising:

acquiring accident data performed by an Emergency Medical Services (EMS) team or first responder at the accident site, including patient information, brief description of accident site, and any witnesses or family information;

entering said accident data into an on-site computer via video camera and speech recognition software;

transferring said accident data from the on-site computer to a Central Medical Facility (CMF) computer;

analyzing said accident data by an emergency healthcare provider;

developing a Cardiac Arrest (CA) diagnosis of a patient by the emergency healthcare provider based upon said accident data;

transferring said CA diagnosis to a second computer located at the ER;

sending orders to administer medication, based on the CA diagnosis, to the EMS team at said accident site;

displaying results of the administration of medication on the on-site computer monitor at the accident site for EMS team to review and continue resuscitation process;

administering medication to the patient using a manual pocket crash cart (PCC) or automatic pocket crash cart (APCC);

wherein, the PCC or APCC includes a plurality of syringes, each containing a type of emergency medication;

wherein the PCC or APCC further includes a multi-port needleless intravenous connector with integrated check valves and tubing including slide clamps to be attached to the patient's intravenous line;

wherein the plurality of syringes are connected to the multi-port needleless intravenous connector;

wherein, the administration of the medication further includes adjusting a volume of the type of emergency medication in each of the plurality of syringes, based on a heart rhythm displayed on a defibrillator connected to the patient.

2. The CAR process of claim 1, wherein said CA diagnosis includes a visual display of the EMS team to the emergency healthcare provider.

3. The CAR process of claim 1, wherein said CA diagnosis includes a real time monitoring of the accident site.

4. The CAR process of claim 1, wherein said acquiring accident data step comprises a defibrillator equipped with a video camera, voice recognition and mirroring display software, access to internet and display for notes.

5. The CAR process of claim 4, wherein the defibrillator is configured to:

display and analyze a heart rhythm to advise for electric shock;

display EMS team communication and transfer the heart rhythm and acquired data from accident site to the on-site computer;

transfer, by the on-side computer, acquired data to the central medical facility for the emergency healthcare provider to review;

display and analyze the heart rhythm;

display communication notes.

6. The CAR process of claim 1, wherein the on-site computer is equipped with a video camera, with voice recognition software, mirroring display software, and access to internet;

wherein, the on-site computer is configured to:

acquire data from the accident site;

transfer data to the CMF computer and receive feedback from the emergency healthcare provider.

7. The CAR process of claim 1, wherein the medication is administered to the patient with a PCC.

8. The CAR process of claim 1, wherein the plurality of syringes at least includes a first syringe filled with epinephrine, a second syringe filled with amiodarone, and a third syringe filled with atropine.

9. The CAR process of claim 8, wherein the multi-port needleless intravenous connector further includes a port attached to a 0.9% normal saline intravenous (IV) bag or syringe for flushing.

10. The CAR process of claim 1, wherein each of the plurality of syringes includes a syringe body with a dose window, a dose indicator, and a dose knob.

11. The CAR process of claim 10, wherein the syringe body includes a cartridge holder and a plunger.

12. The CAR process of claim 1, wherein the medication is administered to the patient with an APCC.

13. The CA process of claim 12, wherein the APCC includes a processor, a display, and a water-resistance case.

14. The CA process of claim 12, wherein the PCC or APCC includes a user interface configured for a user to choose medication and dosage.

15. The CA process of claim 1, wherein the PCC or APCC supports remote administration of the medications.

* * * * *